US006953777B2

(12) United States Patent
Keith et al.

(10) Patent No.: US 6,953,777 B2
(45) Date of Patent: *Oct. 11, 2005

(54) USE OF INTERLEUKIN-11 TO PREVENT IMMUNE-MEDIATED CYTOTOXICITY

(75) Inventors: James Keith, Andover, MA (US); Joseph M. Carroll, Cambridge, MA (US); Jordan S. Pober, Guilford, CT (US)

(73) Assignees: Genetics Indtitute LLC, Cambridge, MA (US); Yale University, New Haven, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/521,696

(22) Filed: Mar. 9, 2000

(65) Prior Publication Data

US 2001/0051600 A1 Dec. 13, 2001

Related U.S. Application Data

(60) Provisional application No. 60/124,024, filed on Mar. 11, 1999.

(51) Int. Cl.[7] .......................... A61K 38/00; A61K 38/21

(52) U.S. Cl. ................................ 514/12; 514/2; 514/8; 514/885; 424/85.1; 424/85.2

(58) Field of Search .......................... 514/2, 8, 12, 885; 424/85.1, 85.2

(56) References Cited

U.S. PATENT DOCUMENTS

| | | | |
|---|---|---|---|
| 4,518,584 A | 5/1985 | Mark et al. .................... | 424/85 |
| 5,215,895 A | 6/1993 | Bennett et al. .......... | 435/69.52 |
| 5,270,181 A | 12/1993 | McCoy et al. .............. | 435/69.7 |
| 5,292,646 A | 3/1994 | McCoy et al. .............. | 435/69.7 |
| 5,460,810 A | 10/1995 | Williams et al. | |
| 5,496,830 A | 3/1996 | Shapiro et al. .............. | 514/283 |
| 5,582,821 A | 12/1996 | Kaye | |
| 5,631,219 A | 5/1997 | Rosenthal et al. .............. | 514/6 |
| 5,679,339 A | 10/1997 | Keith et al. | |
| 5,700,664 A | * 12/1997 | Yang et al. ............... | 435/69.52 |
| 5,846,958 A | 12/1998 | Capizzi et al. ............... | 514/114 |
| 5,854,028 A | 12/1998 | Yang et al. .............. | 435/69.52 |
| 6,066,317 A | 5/2000 | Yang et al. | |
| 6,126,933 A | 10/2000 | Warne et al. | |

FOREIGN PATENT DOCUMENTS

| | | |
|---|---|---|
| WO | WO 92/04455 | 3/1992 |
| WO | WO 96/19574 | 6/1996 |
| WO | WO 97/01353 | 1/1997 |
| WO | WO 99/37322 | 7/1999 |
| WO | WO 00/74707 | 12/2000 |

OTHER PUBLICATIONS

Hill et al., Interleukin–11 Promotes T Cell Polarization and Prevents Acute Graft–Versus_Host Disease after Allogeneic Bone Marrow Transplantation. J.Clin.Invest. vol. 102 (1), 115–123.*
Hill, *IL–11 Promotes T Cell Polarization and Prevents Acute Graft Versus Host Disease After Allogeneic Bone Marrow Transplantation*, 1998, J Clin Invest 102: 115–23.
Biederman, *Human Endothelial Cells Induce and Regulate Cytolytic T Cell Differentiation*, 1998, J Immunol 161: 4679–87.
Du, *Protective Effects of Interleukin–11 in a Murine Model of Ischemic Bowel Necrosis*, 1997, Am J Physiol 272: G545.
Orazi, *Interleukin–11 Prevents Apoptosis and Accelerates Recovery of Small Intestinal Mucosa in Mice Treated with Combined Chemotherapy and Radiation*, 1996, Lab Invest 75: 33.
Redlich, *IL–11 Enhances Survival and Decreases TNF Production After Radiation–induced Thoracic injury*, 1996, J Immunol 157: 1705.
Trepicchio, *IL–11 Regulates Macrophage Effector Function Through the Inhibition of Nuclear Factor–8B*, 1997, J Immunol: 5661.
Yang, *Interleukin (IL)–11–mediated Signal Transduction*, 1995, Ann NY Acad Sci 762: 31.
Miyatake, *Complement–fixing Elicited Antibodies are a Major Component in the Pathogenesis of Xenograft Rejection*, 1998, J Immunol 160: 4114.
Boulton, *STAT3 Activation by Cytokines Utilizing gp130 and Related Transducers Involoves a Secondary Modification Requiring an H7–sensitive Kinase*, 1995, Proc Natl Acad Sci USA 92: 6915.
Pober, *The Role of Endothelial Cells in Inflammation*, 1990, Transplantation 50: 537.
Johnson, *A Sustained Reduction in I 8B–2 May Contribute to Persistent NF–8B Activation in Human Endothelial Cells*, 1996, J Biol Chem 271: 16317.
Ambrosini, *A Novel Anti–apoptosis Gene, Survivin, Expressed in Cancer and Lymphoma*, 1997, Nat Med 3: 917–21.
Reed, *Survivin' Cell–separation Anxiety*, 1999, Nat Cell Biol 1: E199–200.
Chen, *Interleukin–6 Inhibits Transforming Growth Factor–2–induced Apoptosis through the Phosphatidylinositol 3–Kinase/Akt and Signal Transducers and Activators of Transcription 3 Pathways*, 1999, J Biol Chem 274: 23013–19.
Tran, *Marked Induction of the IAP Family Antiapoptotic Proteins Survivin and XIAP by VEGF in Vascular Endothelial Cells*, 1999, Bioch m Biophys Res Commun 264: 781–88.

(Continued)

Primary Examiner—Janet Andres
Assistant Examiner—Jegatheesan Seharaseyon
(74) Attorney, Agent, or Firm—Ivor R. Elrifi, Esq.; Mintz Levin Cohn Ferris Glovsky & Popeo, PC (57) ABSTRACT

The use of interleukin-11 to prevent, to ameliorate, and to treat an immune-mediated disease in a mammal in need of such treatment is disclosed.

12 Claims, 3 Drawing Sheets

OTHER PUBLICATIONS

Mantell, *Hyperoxia–induced Cell Death in the Lung—the Correlation of Apoptosis, Necrosis, and Inflammation*, 1999, Ann NY Acad Sci 887: 171–80.

Dorner et al., Interleukin–11, Biological Activity and Clinical Studies. BioDrugs, 8(6):418–29. (Dec. 1997).

* cited by examiner

FIG. 3

USE OF INTERLEUKIN-11 TO PREVENT IMMUNE-MEDIATED CYTOTOXICITY

RELATED APPLICTIONS

This application claims priority to U.S. Ser. No. 60/124,024, filed Mar. 11, 1999. The contents of this application are incorporated herein by reference in their entire.

FIELD OF INVENTION

The present invention relates to the field of prevention and treatment of immune-mediated disorders using interleukin-11. More particularly, the present invention relates to preventing or treating graft-versus-host disease and CTL- and/or complement-dependent rejection of organ or tissue transplants using interleukin-11.

BACKGROUND OF THE INVENTION

An individual mammal's immune system functions through recognition of certain cell surface proteins, some of which are termed major histocompatibility complex proteins, or MHC proteins. Additional minor histocompatibility proteins exist which can also contribute to immunological recognition events. The individual mammal's immune system recognizes its own MHC proteins, or those of its identical twin, as self and thus does not destroy its own cells or those of its identical twin. Members of the same species may share major and/or minor histocompatibility antigens, and thus an individual may not recognize the cells of another member of its species as non-self, depending on the degree of the differences between the MHC proteins of the two individuals. When an individual's immune system recognizes the cells of other members of the same species as non-self, the first individual's immune system may proceed to destroy the cells of the second individual. In humans, the major histocompatibility proteins are known as "HLA" antigens.

When tissues such as bone marrow, blood cells, or solid organs are transplanted from one individual to another, normally the recipient will recognize the donor's cells as non-self and the recipient's immune system will destroy the donor's cells as described above. For this reason, in a tissue transplantation, the recipient is normally subjected to immunosuppressive drugs and/or irradiation. However, transplantation patients are also subject to immunologic recognition in the opposite direction, that is, the donor tissue may contain immunologically competent cells which proceed to destroy the recipient's cells, a condition termed "graft-versus-host disease" or "GVHD".

Graft-versus-host disease can develop when bone marrow, blood products, or solid organs containing immunocompetent cells are transferred from a donor to a recipient. Thus, when MHC antigenic differences exist between the donor and recipient, the recipient is at risk for the development of graft-versus-host disease. Graft-versus-host disease may also develop when there are antigenic differences between donor and recipient for the minor histocompatibility antigens. Thus, graft-versus-host disease can also develop between MHC-matched persons. Moreover, surgery patents who receive directed blood transfusion, for example, transfusion of blood from an HLA homozygous child to a heterozygous parent, may also develop graft-versus-host disease.

Current approaches to preventing graft-versus-host disease include attempts to eliminate immunocompetent donor cells, for example, by in vitro manipulation of the donor tissue. For example, immunocompetent T cells may be removed from donor bone marrow through physical separation such as by lectin agglutination, or by treatment of the bone marrow with monoclonal antibodies directed to T cells. However, use of bone marrow depleted of T cells is associated with a higher rate of graft failure, which is frequently fatal. Use of T cell depleted bone marrow grafts is also associated with an increased incidence of relapse among the recipients, particularly recipients having chronic myelocytic leukemia.

Another approach to preventing immune-mediated injury is to interrupt the complement cascade (e.g., by depleting C3 with cobra venom factor or by inhibiting the C3 convertase with recombinant soluble CR1). However, antibody depletion has unacceptable risks of over-immunosuppression (i.e., infection), and experimental studies of inhibition of the complement cascade with cobra venom factor or sCR1 show incomplete inhibition. An additional drawback to the use of cobra venom is the prospect of systemic effects due to the large amounts of vasoactive and chemotactic C3a and C5a produced.

Another common practice for inhibiting immune-mediated disorders is to subject the recipient to immunosuppressive therapy after transplantation. Such immunosuppression may occur by use of glucocorticoids, cyclosporin, methotrexate, or combinations of such drugs. However, immunosuppression also results in increased incidence of infection, and even when immunosuppressant drugs are used, immune-mediated cytotoxicity may still occur.

Although many approaches to controlling immune-mediated disorders have been attempted, none of these approaches have been particularly successful. Thus there remains a need for an effective, clinically applicable means of preventing or treating GVHD and CTL- and/or complement-dependent rejection of organ or tissue transplants.

BRIEF SUMMARY OF THE INVENTION

Surprisingly, the inventors have found that IL-11 demonstrates the ability to protect endothelial cells from immune-mediated injury. Cells pretreated with IL-11 demonstrate a significant decrease in both cytotoxic T cells (CTL) and complement-mediated cytotoxicity over cells which are not pretreated with IL-11. The addition of IL-11 to vascular endothelial cells resulted in activation of signal transducer and activators of transcription protein (STAT) and mitogen activated protein kinase (MAPK) signaling pathways. These studies indicate that IL-11 can protect endothelial cells from immune-mediated injury and may play a role in preventing CTL and complement-dependent rejection of organ or tissue transplants. IL-11 can also protect endothelial cells from non-immune-mediated cytotoxicity, such as necrosis caused by loss of blood supply, corrosion, burning, or the local lesion of a disease.

Provided by the invention are methods of treating disorders where protection against CTL and/or complement-mediated cytotoxicity are shown to be beneficial including, without limitation, graft versus host disease (GVHD), and rejection of organ or tissue transplants. In addition, provided by the present invention are methods of treating non-immune-mediated necrotic injuries, such as localized tissue or cell injury caused by loss of blood supply, corrosion, burning, or the local lesion of a disease.

According to the invention, IL-11, analogs, and derivatives thereof, are administered to patients, either prophylactically or at the onset of symptoms associated with the aforementioned disorders. IL-11 can be administered in suitable pharmaceutically acceptable carriers either alone or in combination with other conventional agents useful in alleviating the symptoms associated with the aforementioned disorders.

In one embodiment, the invention comprises a method of preventing an immune-mediated disease which comprises administering to a mammal, prior to exposure to foreign cell surface proteins, a therapeutically effective amount of interleukin-11.

In another embodiment, the invention comprises a method of ameliorating an immune-mediated disease which comprises administering to a mammal, at the time of exposure to foreign cell surface proteins, a therapeutically effective amount of interleukin-11.

In another embodiment, the invention comprises a method of treating an immune-mediated disease which comprises administering to a mammal experiencing an immune-mediated disease a therapeutically effective amount of interleukin-11.

In preferred embodiments, the therapeutic dose is effective to prevent, ameliorate or treat an immune-mediated disease resulting from exposure to foreign cell surface proteins, such as donor major and/or minor histocompatibility antigens. Preferably, the therapeutically effective amount of interleukin-11 comprises 1 to 100 μg/kg body weight.

Methods are also provided for preventing non-immune mediated necrotic disorders which comprises administering to a mammal, prior to or at the time of local tissue injury, a therapeutically effective amount of interleukin-11. Preferably, the therapeutically effective amount of interleukin-11 comprises 1 to 100 μg/kg body weight. In preferred embodiments, the therapeutic dose is also effective to prevent, ameliorate or treat non-immune mediated disorders resulting from such injury.

DETAILED DESCRIPTION OF THE INVENTION

The following abbreviations are used herein: graft-versus-host disease (GVHD); endothelial cell (EC); human umbilical vein endothelial cell (HUVEC); interleukin-11 (IL-11); recombinant human IL-11 (rhIL-11); activators of transcription protein (STAT); interleukin-12 (IL-12); tumor necrosis factor (TNF); mitogen-activated protein kinase (MAPK); nuclear factor-κB (NF-κB); intracellular adhesion molecule-1 (ICAM-1); major histocompatibility complex (MHC); cytotoxic T lymphocytes (CTL); Janus kinase (JAK); phospho-STAT1 (P-STAT1); and phospho-STAT3 (P-STAT3).

Provided by the present invention are methods of treating disorders where protection against CTL and/or complement-mediated cytotoxicity are shown to be beneficial including, without limitation, GVHD, and rejection of organ or tissue transplants. In addition, provided by the present invention are methods of treating non-immune-mediated necrotic injuries, such as localized tissue or cell injury caused by loss of blood supply, corrosion, burning, or the local lesion of a disease.

IL-11 is a stromal cell-derived pleiotropic cytokine which interacts with a variety of hematopoietic and non-hematopoietic cell types. Recombinant human IL-11 stimulates megakaryocytopoiesis in vitro and in vivo. Weich, N. S., et al. (1997) Blood 90:3893–3902; and Orazi, A., et al. (1996) Exp. Hematol. 24:1289–1297. IL-11 also stimulates erythropoiesis and regulates macrophage proliferation and differentiation. de Haan, G., et al. (1995) Br. J. Haematol. 90:783–790. Due to its thrombopoietic activities in vivo, IL-11 is used to treat chemotherapy-induced thrombocytopenia. Kaye, J. A. (1996) Curr. Opin. Hematol. 3:209–215.

In addition to its hematopoietic effects, IL-11 also protects against various forms of mucosal epithelial cell injury. For example, IL-11 has been shown to protect small intestinal cells from combined radiation, chemotherapy, and ischemia (Du, X., et al. (1997) Am. J. Physiol. 272:G545-G552; Orazi, A., et al. (1996) Lab. Invest. 75:33–42; and Keith, J. C., Jr., et al. (1994) Stem. Cells. (Dayt). 1(12):79–89); reduce experimental colitis induced by trinitrobenzene sulfonic acid in rat (Qiu, B. S., et al. (1996) Dig. Dis. Sci. 41:1625–1630); and ameliorate inflammatory bowel disease (Orazi, A., et al. (1996) Lab. Invest. 75:33–42). The foregoing studies show that treatment with IL-11 decreases mucosal damage, accelerates healing and improves host survival. IL-11 also reduces immune-mediated small bowel injury in acute GVHD following murine allogenic bone marrow transplantation. Hill, G. R., et al. (1998) J. Clin. Invest. 102:115–123.

IL-11 has also been shown to improve survival and decrease TNF production after radiation-induced thoracic injury. Redlich, C. A., et al. (1996) J. Immunol. 157:1705–1710. Human IL-11, expressed as a transgene in bronchial mucosa, reduces mortality associated with hyperoxia in mice. Waxman, A. B., et al. (1998) J. Clin. Invest. 101:1970–1982. This enhanced murine survival may result from reduced lung injury, including alveolar-capillary protein leak, endothelial and epithelial cell membrane injury, lipid peroxidation, pulmonary neutrophil recruitment, IL-12 and TNF production, and DNA fragmentation.

The mechanisms by which IL-11 protects mucosal membranes are not fully understood. IL-11's anti-inflammatory effects are believed to result, at least in part, from down-regulation of various proinflammatory cytokines. Leng, S. X. and J. A. Elias (1997) J. Immunol.159:2161–2168; Trepicchio, W. L., et al. (1997) J. Immunol. 159:5661–5670; and Trepicchio, W. L., et al. (1996) J. Immunol. 157:3627–3634. IL-11 may also cause immune deviation from a $T_H1$-like to a $T_H2$-like phenotype, thereby alleviating immune-mediated injury. Hill, supra.

IL-11 belongs to the interleukin-6 (IL-6) family of cytokines, all of which use gp130 as a critical component for signal transduction. Taga, T. and T. Kishimoto (1997) Annu. Rev. Immunol. 15:797–819; Zhang, X. G., et al. (1994) J. Exp. Med. 179:1337–1342; and Yang, Y. C. and T. Yin (1995) Ann. N.Y. Acad. Sci. 762:31–40. IL-11 initiates signaling via binding to a unique IL-11-receptor-α (IL-11Rα) chain. Nandurkar, H. H., et al. (1996) Oncogene 12:585–593; Miyatake, T., et al. (1998) J. Immunol. 160:4114–4123. The IL-11/IL-11Rα complex is thought to bind to and induce clustering gp130, leading to the activation, via transphosphorylation, of associated JAKs. Yin, T., K., et al. (1994) Exp. Hematol. 22:467–472; Wang, X. Y., et al. (1995) J. Biol. Chem. 270:27999–28002. Activated JAKs phosphorylate tyrosine residues within the cytoplasmic region of gp130 which then serve as docking sites for signal transducer and activators of transcription proteins, STAT3 and STAT1. Lutticken, C., et al. (1994) Science 263:89–92; Hemmann, U., et al. (1996) J. Biol. Chem. 271:12999–13007. The activated JAKs subsequently phosphorylate tyrosine residues within the bound STAT proteins, causing the STATs to dissociate from gp130, dimerize, and enter the nucleus to act as transcriptional activators of target genes. Zhong, Z., et al. (1994) Science 264:95–98; Ihle, J. N. (1996) Cell 84:331–334; and Akira, S. (1997) Int. J. Biochem. Cell Biol. 29:1401–1418. STAT dimers may be additionally phosphorylated on serine orthreonine residues by mitogen activated protein kinases (MAPKs) that are also activated in response to cytokine binding to the receptor. Zhang, X., et al. (1995) Science 267:1990–1994; Boulton, T. G., et al. (1995) Proc. Natl. Acad. Sci. U.S.A. 92:6915–6919; Adunyah, S. E., et al. (1995) Ann. N.Y. Acad. Sci. 766:296–299; and Yin, T. and Y. C. Yang (1994) J. Biol. Chem. 269:3731–3738. This additional phosphorylation may potentiate STAT function as an activator of transcription.

IL-11 is described in detail in International Application PCT/US90/06803, published May 30, 1991; as well as in U.S. Pat. No. 5,215,895; issued Jun. 1, 1993. A cloned human IL-11 was previously deposited with the ATCC, 10801 University Boulevard, Manassa, Va. 20110-2209, on Mar. 30, 1990 under ATCC No. 68284. Moreover, as described in U.S. Pat. No. 5,270,181; issued Dec. 14, 1993; and U.S. Pat. No. 5,292,646; issued Mar. 8, 1994; IL-11 may also be produced recombinantly as a fusion protein with another protein. IL-11 can be produced in a variety of host cells by resort to now conventional genetic engineering techniques. In addition, IL-11 can be obtained from various cell lines, for example, the human lung fibroblast cell line, MRC-5 (ATCC Accession No. CCL 171) and Paul et al., the human trophoblastic cell line, TPA30-1 (ATCC Accession No. CRL 1583). Described in Proc Natl Acad Sci USA 87:7512 (1990) is a cDNA encoding human IL-11 as well as the deduced amino acid sequence (amino acids 1 to 199). U.S. Pat. No. 5,292,646, supra, describes a des-Pro form of IL-11 in which the N-terminal proline of the mature form of IL-11 (amino acids 22–199) has been removed (amino acids 23–199). As is appreciated by one skilled in the art, any form of IL-11, which retains IL-11 activity, is useful according to the present invention.

In addition to recombinant techniques, IL-11 may also be produced by known conventional chemical synthesis. Methods for constructing the polypeptides useful in the present invention by synthetic means are known to those of skill in the art. The synthetically constructed cytokine polypeptide sequences, by virtue of sharing primary, secondary, or tertiary structural and conformational characteristics with the natural cytokine polypeptides are anticipated to possess biological activities in common therewith. Such synthetically constructed cytokine polypeptide sequences or fragments thereof, which duplicate or partially duplicate the functionality thereof may also be used in the method of this invention. Thus, they may be employed as biologically active or immunological substitutes for the natural, purified cytokines useful in the present invention.

Modifications in the protein, peptide or DNA sequences of these cytokines or active fragments thereof may also produce proteins which may be employed in the methods of this invention. Such modified cytokines can be made by one skilled in the art using known techniques. Modifications of interest in the cytokine sequences, e.g., the IL-11 sequence, may include the replacement, insertion or deletion of one or more selected amino acid residues in the coding sequences. Mutagenic techniques for such replacement, insertion or deletion are well known to one skilled in the art. (See, e.g., U.S. Pat. No. 4,518,584.)

Other specific mutations of the sequences of the cytokine polypeptides which may be useful therapeutically as described herein may involve, e.g., the insertion of one or more glycosylation sites. An asparagine-linked glycosylation recognition site can be inserted into the sequence by the deletion, substitution or addition of amino acids into the peptide sequence or nucleotides into the DNA sequence. Such changes may be made at any site of the molecule that is modified by addition of O-linked carbohydrate. Expression of such altered nucleotide or peptide sequences produces variants which may be glycosylated at those sites.

Additional analogs and derivatives of the sequence of the selected cytokine which would be expected to retain or prolong its activity in whole or in part, and which are expected to be useful in the present method, may also be easily made by one of skill in the art. One such modification may be the attachment of polyethylene glycol (PEG) onto existing lysine residues in the cytokine sequence or the insertion of one or more lysine residues or other amino acid residues that can react with PEG or PEG derivatives into the sequence by conventional techniques to enable the attachment of PEG moieties.

Additional analogs of these selected cytokines may also be characterized by allelic variations in the DNA sequences encoding them, or induced variations in the DNA sequences encoding them. It is anticipated that all analogs disclosed in the above-referenced publications, including those characterized by DNA sequences capable of hybridizing to the disclosed cytokine sequences under stringent hybridization conditions or non-stringent conditions (Sambrook et al., Molecular Cloning. A Laboratory Manual, 2d edit., Cold Spring Harbor Laboratory, New York (1989)) will be similarly useful in this invention.

Also considered useful in these methods are fusion molecules, prepared by fusing the sequence or a biologically active fragment of the sequence of one cytokine to another cytokine or proteinaceous therapeutic agent, e.g., IL-11 fused to IL-6 (see, e.g., methods for fusion described in PCT/US91/06186 (WO92/04455), published Mar. 19, 1992). Alternatively, combinations of the cytokines may be administered together according to the method.

Thus, where in the description of the methods of this invention IL-11 is mentioned by name, it is understood by those of skill in the art that IL-11 encompasses the protein produced by the sequences presently disclosed in the art, as well as proteins characterized by the modifications described above yet which retain substantially similar activity. Standard laboratory tests are utilized to monitor progress of the treatment Decreased symptomatology could also be used to monitor the effectiveness of treatment as is well known to physicians skilled in the art of treating such disorders.

For use in the method of the invention, a therapeutically effective amount of IL-11 is administered to a mammal at risk of developing an immune-mediated disorder. As used herein, the phrases "immune-mediated disorder" and "immune-mediated disease", which are used interchangeably, mean any disorder or disease characterized by CTL and/or complement-mediated cytotoxicity or cytolysis. For example, an immune-mediated disorder may result when a tissue transplant is donated by an individual whose genetic characteristics differ from those of the recipient, especially as regards the MHC and minor histocompatibility antigens expressed on the surfaces of each individual's cells. If the recipient's immune system recognizes the donor's cells as non-self, the recipient's immune system will destroy the donor's cells. An immune-mediated disorder or disease may also result from immunologic recognition in the opposite direction, that is, when the donor tissue contains immunologically competent cells which proceed to destroy the recipient's cells, such as in GVHD.

The present invention also contemplates the administration of a therapeutically effective amount of IL-11 to a mammal at risk of developing a non-immune-mediated disease or disorder. As used herein, the phrases "non-immune-mediated disorder" and "non-immune-mediated disease" are used interchangeably to refer to a condition characterized by necrotic injury, such as the localized tissue or cell injury caused by loss of blood supply, corrosion, burning, or the local lesion of a disease.

As used herein, the term "complement" means a complex group of proteins and glycoproteins found in the blood of vertebrates. These proteins function in the production of inflammation, opsonize foreign materials for phagocytosis, and mediate direct cytotoxicity against various cells. Complement action against cells proceeds by activation of a protease called C3 convertase via one of two pathways: the classic pathway, where binding to an antigen-antibody complex involving IgG or IgM activates C1 which cleaves C2 and C4 to produce a protease that activates C3 by cleaving it to produce C3b; or the alternative pathway, where C3b is produced by a C3 converting protease formed from other complement factors, including Factors B, D, and P, activated by other activators, such as bacterial endotoxin, certain polysaccharides or complexes of antigen with other antibodies. C3b, in complex with activated C2 and C4 or with activated Factor B and P, cleaves C5 to produce C5b which combines sequentially with C6, C7, C8, and C9 to form the "membrane attack complex" (MAC) that is capable of damaging biological membranes.

As used herein, the term "tissue" means an aggregate of mammalian cells which may constitute a solid mass or a suspension of cells, such as blood cells, or a mammalian cell line.

As used herein, the term "therapeutically effective amount" means the total amount of each active component of the pharmaceutical composition or method that is sufficient to show a meaningful patient benefit, e.g., a reduction in the incidence or severity of acute or chronic graft-versus-host disease compared to that expected for a comparable group of patients not receiving interleukin-11, as determined by the attending physician. When applied to an individual active ingredient administered alone, the term refers to that ingredient alone. When applied to a combination, the term refers to combined amounts of the active ingredients that result in the therapeutic effect, whether administered in combination, serially, or simultaneously.

In practicing the method of the present invention, a therapeutically effective amount of IL-11 is administered to a mammal at risk of developing an immune-mediated disorder. The IL-11 may be administered in accordance with the method of the invention either alone or in combination with other therapies such as treatments employing T cell-depleted autologous or syngeneic bone marrow, immunosuppressive drugs, cytokines, lymphokines, or other hematopoietic factors.

When co-administered with T-cell-depleted autologous or syngeneic bone marrow, immunosuppressive drugs, one or more cytokines, lymphokines, or other hematopoietic factors, the IL-11 may be administered either simultaneously with the T-cell-depleted autologous or syngeneic bone marrow, immunosuppressive drugs, cytokine(s), lymphokine(s), other hematopoietic factor(s), or sequentially. If administered sequentially, the attending physician will decide on the appropriate sequence of administering the IL-11 in combination with the T-cell depleted autologous or syngeneic bone marrow, immunosuppressive drugs, cytokine(s), lymphokine(s), and other hematopoietic factor(s).

Administration of the interleukin-11 used to practice the method of the present invention can be carried out in a variety of conventional ways, such as oral ingestion, inhalation, or cutaneous, subcutaneous, or intravenous injection. Intravenous or subcutaneous administration to the patient is preferred.

When a therapeutically effective amount of interleukin-11 is administered orally, the interleukin-11 will be in the form of a tablet, capsule, powder, solution or elixir. When administered in tablet form, the pharmaceutical composition of the invention may additionally contain a solid carrier such as a gelatin or an adjuvant. The tablet, capsule and powder contain from about five to 95% interleukin-11, preferably from about 25–90% interleukin-11. When administered in liquid form, a liquid carrier such as water, petroleum, oils of animal or plant origins such as peanut oil, mineral oil, soy bean oil, or sesame oil, or synthetic oils, may be added. The liquid form of the pharmaceutical composition may further contain physiological saline solution, dextrose, or other saccharide solutions, or glycols such as ethylene glycol, propylene glycol or polyethylene glycol. When administered in liquid form, the pharmaceutical composition contains about 0.5 to 90% by weight of interleukin-11 and preferably from about 1 to 50% interleukin-11.

When a therapeutically effective amount of interleukin-11 is administered by intravenous, cutaneous or subcutaneous injection, the interleukin-11 will be in the form of a pyrogen-free, parenterally-acceptable aqueous solution. The preparation of such parenterally-acceptable protein solutions, having due regard to pH, isotonicity, stability, and the like, is within the skill in the art. A preferred pharmaceutical composition for intravenous, cutaneous, or subcutaneous injection should contain, in addition to interleukin-11, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition for use in the present method may also contain stabilizers, preservatives, buffers, antioxidants, or other additive known to those with skill in the art. It is contemplated that the pharmaceutical composition used to practice the method of the present invention should contain about 0.1 pg to about 100 mg of interleukin-11 per ml of solution, preferably about 0.1 mg of interleukin-11 per ml of solution.

In practicing the method of preventing or ameliorating an immune-mediated disease in accordance with the present invention, it is contemplated that the duration of the application of IL-11 will be in the range of 12–48 hours of continuous or intermittent subcutaneous or intravenous administration, beginning prior to or at the time of tissue transplantation. For the purpose of the present invention, "at the time of tissue transplantation" is defined as being during the 1 hour period before or the 1 to 24 hour period after the transplantation. In a preferred embodiment, IL-11 is administered beginning at least 24 hours prior to the time of tissue transplantation. As an example of a method for preventing or ameliorating graft-versus-host disease, preferably 1 µg/kg to 100 µg/kg of IL-11 may be administered daily to the mammal, more preferably 1 µg/kg to 75 µg/kg of IL-11 may be administered daily to the mammal, and most preferably 1 µg/kg to 15 µg/kg may be administered daily to the mammal. In one preferred dosage regimen, the first dose of IL-11 is given one hour after tissue transplantation and two more doses are given on days one and two post-transplant. Alternative treatment regimens may be appropriate for individual patients and will be determined by the attending physician, taking into account the nature and severity of the condition being treated, and the nature of the prior treatments which the patient has undergone.

Modifications of the treatment regimen set forth above for prevention or ameliorating an immune-mediated disease may be made for treatment of ongoing acute or chronic disease. For the purpose of the present invention, "acute" disease is defined as occurring during the time period from three days to 100 days post transplantation in humans; and "chronic" disease is defined as occurring at any time after 100 days post-transplantation in humans. As an example of a method for treating ongoing acute or chronic graft-versus-host disease, 1 µg/kg to 100 µg/kg may be administered daily to a mammal experiencing acute or chronic graft-versus-host disease, until improvement or remission of the symptoms of acute or chronic graft-versus-host disease is observed. Ultimately, the attending physician will decide on the appropriate duration of subcutaneous or intravenous therapy using the pharmaceutical composition of IL-11 in the method of the present invention.

As shown in the Examples herein, IL-11 has a direct effect on vascular EC. Cultured HUVECs express IL-11Rα as well as gp130, and stimulation of HUVECs with IL-11 induces rapid phosphorylation of gp130, STAT3, STAT1, and p42/p44 MAPKs. In addition, IL-11 pretreatment induces HUVECs to become resistant to injury mediated by CTL or by antibody plus complement. IL-11 does not inhibit proinflammatory response of HUVECs to TNF, such as NF-κB activation or adhesion molecule expression. These data provide the first in vitro evidence of a direct cytoprotective actions of IL-11 and do not support an anti-inflammatory effect of this cytokine on endothelium. A similar lack of anti-inflammatory effect is observed for IL-11 when LPS rather than TNF was used as stimulus for endothelial activation (unpublished observations).

Functional receptor complexes for IL-6 family of cytokines including IL-11, oncostatin M, and IL-6 share gp130 as a component critical for signal transduction. Zhang, X. G., et al. (1994) J. Exp. Med. 179:1337–1342; and Yang, Y. C. and T. Yin (1995) Ann. N. Y. Acad. Sci. 762:31–40. IL-11 binds to IL-11Rα chain on the cell surface, and IL-11/IL-11R complex then associate with gp130, causing it cluster. This is essentially the same mechanism of action that has been observed for IL-6/IL-6R signaling. Oncostatin M differs from IL-11 and IL-6 in that it directly binds to gp130 and signals through either gp130/leukemia inhibitory factor receptor β or gp130/oncostatin M receptor heterodimers. Renne, C., et al. (1998) J. Biol. Chem. 273:27213–27219; and Auguste, P., et al. (1997). Because gp130 is ubiquitously expressed, the responsiveness of cells to a particular cytokine of IL-6 family is determined by the relative expression of other receptor component. Among receptors for IL-6 family of cytokines, endothelial cells lack IL-6Rα chain (Romano, M., et al. (1997) Immunity. 6:315–325) but express receptors for leptin (Sierra-Honigmann, M. R., et al. (1998) Science 281:1683–1686) and oncostatin M. Brown, T. J., et al. (1991) J. Immunol. 147:2175–2180; Frasca, D., et al. (1996) Int. Immunol. 8:1651–1657; and Schieven, G. L., et al. (1992) J. Immunol. 149:1676–1682. As shown previously, endothelial cells respond to oncostatin M with activation of MAPK activity (Faris, M., et al. (1998) AIDS 12:19–27), IL-6 secretion (Brown, T. J., et al. (1991) J. Immunol. 147:2175–2180), P-selectin (Yao, L., et al. (1996) J. Exp. Med. 184:81–92), ICAM-1 and E-selectin synthesis (Modur, V., et al. (1997) J. Clin. Invest. 100:158–168, and increased growth (Faris, 1998, supra). Surprisingly, compared to IL-11, oncostatin M is a very strong inducer of gp130, STAT3, STAT1, and MAPK phosphorylation in HUVECs. This greater potency of oncostatin M may also explain why oncostatin M but not IL-11 appears to activate pro-inflammatory functions of HUVECs. Modur, V., et al. (1997) J. Clin. Invest. 100:158–168; Yao, L., et al. (1996) J. Exp. Med. 184:81–92. It also does not appear to be mitogen for HUVECs (unpublished observations). Thus, not all gp130 signaling cytokines induce the same biological responses in EC, and some differences may relate to signal strength.

As shown in the Examples herein, cytoprotection of HUVECs is protein-synthesis dependent. Although not wishing to be bound by theory, it is believed that IL-11 induces new or increases expression of a cytoprotective protein. Activation of transcription factors STAT and MAPKs may play a role in the induction of these cytoprotective proteins. Surprisingly, concentrations of IL-11 that confer the most significant cytoprotection activate STAT3 and MAPKs but not STAT1 in HUVECs. Conceivably, low doses of IL-11 produce primarily STAT3 heterodimers which translocate into the nucleus and mediate the cytoprotective effects of IL-11. However, STAT1 activation by high dose of IL-11 may antagonize the IL-11-mediated cytoprotection, by formation of STAT3/STAT1 heterodimes.

Cytotoxic CD8$^+$ T lymphocytes can recognize and kill appropriate allogenic targets by direct contact. Shresta, S., et al. (1998) Curr. Opin. Immunol. 10:581–587. Target cell killing by CTL involves specific recognition of Class I MHC-peptide complex on the target cell by T cell receptor. LFA3 and ICAM-1 or ICAM-2 expressed on the target cells facilitate CTL-target cell recognition by enhancing cell-cell contact. CTL can not efficiently recognize and kill target cells which do not express class I MHC, LFA3, or ICAM-1. As shown in the Examples below, IL-11 significantly protects HUVECs against lysis by allospecific CTLs without effecting the expression of either class I MHC or ICAM-1 on these cells. LFA3 levels are also unaffected (unpublished observations). Thus the mechanism of protection probably follows conjugate formation. Bound CTL deliver a lethal hit by two different mechanisms: granule exocytosis, also known as the perforin/granzyme B pathway, and Fas/Fas ligand (FasL) signaling. Shresta, S., et al. (1998) Curr. Opin. Immunol. 10:581–587. HUVECs can not be killed through Fas engagement by Fas ligand. Richardson, B. C., (1994) Eur. J. Immunol. 24:2640–2645; unpublished observations. Perforin, a protein that is similar to the C9 terminal component, and granzyme B are present within the cytotoxic granules of CTL. Shinkai, Y., et al. (1998) Nature 334:525–527; Krahenbuhl, O. and J. Tschopp (1990) Nat. Immun. Cell Growth. Regul. 9:274–282. When the activated CTL binds to its target, it degranulates, depositing perforin on the target cell membrane where it forms pores. Granzyme B enters the pores and initiates apoptosis. Complement also forms pores in target cell membrane, but does not typically initiate apoptosis. We speculate that the common mechanism of protection vs CTL and complement is the induction of a protein which can inhibit formation of membrane pores or promote their loss by vesiculation or endocytosis. It should be pointed out that the usual protective protein on human cells that disassembles complement pores (e.g. CD59) is not operative against perforin or against heterologous rabbit complement.

Material & Methods

Cytokines and Antibodies:

Recombinant human IL-11, neutralizing antibody (Ab) to IL-11, and anti-IL-11 receptor α chain Ab were provided by Genetics Institute (Andover, Mass.). Recombinant human oncostatin M and recombinant human IFN-γ were purchased from R&D Systems (Minneapolis, Minn.). Recombinant human TNF was a gift from Biogen Inc. (Cambridge, Mass.). Abs reactive with STAT1, phosphotyrosine-STAT1, STAT3, phosphotyrosine-STAT3, p42 and p44 MAPK, and phosphothreonine/phosphotyrosine-p42 and p44 MAPK were purchased from New England Biolabs Inc. (Beverly, Mass.). Anti-human gp130 and anti-phosphotyrosine Abs were purchased from Upstate Biotechnology (Lake Placid, N.Y.) and anti-IκBα Ab was obtained from Santa Cruz Biotechnology (Santa Cruz, Calif.). Anti-class I MHC antibody (W6/32) was prepared as ascites in our laboratory from a clone provided by Dr. Jack Strominger (Harvard University, Cambridge, Mass.). and FITC-conjugated anti-human class I MHC mAb (W6/32) was purchased from Serotech (Oxford, England). Mouse anti-human-E-selectin mAb (clone H14/18) and non-blocking (K16/16) Ab were made as ascites in our laboratory. Mouse anti-human-ICAM1 mAb (E16) was a gift from Dr. Dario Altieri (Yale University, New Haven, Conn.). FITC-conjugated goat anti-mouse Ab was purchased from Boehringer Mannheim (Indianapolis, Ind.). Baby rabbit complement was purchased from Pel-Freez (Brown Dear, Wis.)

Cell Isolation:

Human EC were isolated from umbilical veins as previously described. Gimbrone, M. A., Jr. (1976) Prog. Hemost. Thromb. 3:1–28; Thornton, S. C., et al. (1983) Science 222:623–625), and cultured on gelatin-coated tissue culture plastic (J. T. Baker, Phillipsburg, N.J.) at 37EC in 5% $CO_2$-humidified air in Medium 199 containing 20% FBS, 2 mM L-glutamine, 100 U/ml penicillin, 100 μg/ml streptomycin (all from Life Technologies, Grand Island, N.Y.) 50 μg/ml of endothelial cell growth factor (Collaborative Research/Becton Dickinson, Bedford, Mass.) and 100 μg/ml of porcine intestinal heparin (Sigma, St. Louis, Mo.). K562 cells were obtained from the American Type Culture Collection (Rockville, Md., Accession number: CCL-243) and cultured at 37EC in 5% $CO_2$-humidified air in RPMI 1640 medium (Life Technologies, Grand Island, N.Y.) containing 10% FBS, 2 mM L-glutamine, 100 U/ml penicillin, and 100 μg/ml streptomycin.

Ribonuclease Protection Assay (RPA):

RNA was harvested from HUVECs and K562 cells using the RNAeasy kit (Qiagen, Santa Clarita, Calif.) and 4 μg of each RNA was incubated overnight with a $^{32}$P-labeled probe cocktail against human-IL-11Rα chain and glyceraldehyde phosphate dehydrogenase (GAPDH) as loading control (Riboquant kit and custom template, Pharmingen, San Diego, Calif.). Hybridization reactions were incubated over night at 56EC and then digested with RnasA/T1 and proteinase K (321 bp for IL-11Rα and 96 bp for GAPDH). Protected fragments were precipitated and were separated using a 6% acrylamide Tris-borate EDTA (TBE)-urea gel, and then visualized by autoradiography (Western Blot). In both cell types, a single band at about 80–83 kD representing the human-IL-11Rα chain was detected by SDS-PAGE.

Immunoprecipitation and Immunoblotting:

To analyze protein by immunoblotting of cultured cell lysates, cells (ECs and K562) were washed twice with ice-cold phosphate buffered saline (PBS) containing 1 mM sodium orthovanadate and 1 mM sodium fluoride and were then lysed in a 100 μl of cold RIPA lysis buffer (PBS, 1% NP40, 0.5% sodium deoxycholate, 0.1% SDS, 1 mM PMSF, 10 μg/ml leupeptin, 1 mM sodium orthovanadate). Cell lysates were clarified by centrifugation at 10,000×g for 15 min, and protein concentrations of the supernatant were determined by using a Bio-Rad assay kit (Bio-Rad, Hercules, Calif.). Lysates were prepared for SDS-polyacrylamide gel electrophoresis (SDS-PAGE) by adding an equal volume of 2×SDS-PAGE sample buffer (100 mM Tris-Cl, pH 6.8, 200 mM dithiothreitol, 4% SDS, 0.2% bromophenol blue, 20% glycerol) and heating the mixture in a boiling water bath for 3 min. 10 μg aliquots of cell lysate were resolved by SDS-PAGE using 8% acrylamide gels and a Tris-glycine electrophoresis buffer system (25 mM Tris, 250 mM glycine, 0.1% SDS, pH 8.3) and separated proteins were transferred to a PVDF membrane by electrophoresis (Immobilon P, Millipore). Membranes were incubated with blocking solution containing 5% non-fat dry milk in Tris Buffer Saline Tween (TBST) (10 mM Tris-HCl, pH 8.0, 0.150 mM NaCl, 0.05% Tween 20) at room temperature for 30 min followed by incubation with TBST containing the indicated Ab overnight at 4EC. Membranes were washed and incubated with a suitable horse raddish peroxidase (HRP)-conjugated detecting reagent (Jackson Immuno Research, West Grove, Pa.) and HRP activity was detected using an enhanced chemiluminescence (ECL) kit according to the manufacturer's instructions (Pierce, Rockford, Ill.).

For immunoprecipitation prior to immunoblotting of gp130, 500 μg of total cell lysate was precleared by incubation with 4 μg of rabbit IgG for 90 min on rotator at room temperature, followed by addition of 50 μl of GammaBind G sepharose beads (Pharmacia, Piscataway, N.J.) with continual incubation on a rotator at room temperature for an additional 90 min. The beads were removed from the precleared lysates by centrifugation. To form specific immune complexes, 4 μg of anti-gp130 Ab was added to the precleared lysate which was then incubated for 90 min on a rotator at room temperature. To collect specific immune complexes, 50 μl of GammaBind G sepharose beads were added and the sample was incubated on a rotator at 4EC overnight at which time beads were collected by centrifugation at 13,000×g for 1 min. The beads containing immune complexes were washed 5 times with PBS, the immune complexes were solubilized from the beads by addition of 1×SDS-PAGE sample buffer and heated in a boiling water bath for 5 min. Aliquots were resolved by SDS-PAGE and immunoblotted for total gp130 and for phosphotyrosine residues, as described above.

Indirect Immunofluorescence and FACS Analysis:

After treatment with cytokines, HUVECs were suspended by washing with Hanks Buffered Saline Solution and incubated for 1 min with Trypsin/EDTA. Detached cells were collected and washed twice with ice cold PBS containing 1% BSA, and incubated with specific primary mAb (either anti-E-selectin, anti-ICAM1, or FITC-conjugated anti-class 1 MHC) for 30 min at 4EC. Replicate aliquots were incubated with non-binding isotype control mAb. Labeled cells were washed twice with PBS/1% BSA were fixed with 2% paraformaldehyde before being analyzed. In the case of E-selectin and ICAM-1-mAb-labeled, cells were incubated with a FITC-conjugated goat-anti-mouse Ab for 30 min on ice followed by washing twice with PBS/1% BSA prior to fixation. After fixation, cells were analyzed on a FACSort Lysis II software (Becton Dickinson). Corrected mean fluorescence values was calculated as follows: for each treatment the mean fluorescence value for the isotype matched non-binding control antibody was subtracted from the mean fluorescence value for the specific antibody.

Transfection and Promoter Reporter Gene Assays:

Transient transfection of HUVECs were performed using a DEAE-dextran protocol as described previously. Karmann, K., et al. (1996) J. Exp. Med. 184:173–182. Cell were transfected with both a κB-luciferase promoter reporter gene, which contains two κB sites from Ig kappa enhancer (Min, W., et al. (1996) Mol. Cell Biol. 16:359–368) and a constitutively active β-galactosidase expression construct (Promega, Madison, Wis.). Cell lysates were assayed for luciferase and β-galactosidase activities using Promega reporter assay system (Promega, Madison, Wis.). Luciferase activity was measured using a Berthold (Schwarzwald, Germany) model LB9501 luminometer, and β-galactosidase was measured spectrophotometrically (at 420 nm). Luciferase values in relative light units were normalized to β-galactosidase units to control for transfection efficiency.

Complement Mediated Lysis:

Target HUVECs were grown in 96-well plates to confluence and incubated with 20 μM calcein-AM (Molecular Probes, Eugene, Oreg.) in Medium 199 and 5 mM HEPES for 30 min at 37 EC. The medium was replaced by complete EC growth medium and cells were rested overnight. IL-11 in media or media alone were added for an addition of 6 h, after which cells were washed twice with Medium 199, 5% FBS, 5 mM HEPES, 2 mM L-glutamine, 100 U/ml penicillin, 100 μg/ml streptomycin. Where indicated, 20 μg/ml of cycloheximide were included during the incubation with IL-11. To initiate cytotoxicity, cells were incubated with anti-class 1 MHC mAb (W6/32) for 30 min at 37EC at indicated concentrations. Baby rabbit complement was then added at the indicated concentrations. To measure the extent of lysis after 1 hr, supernatant was removed and transferred into a flat-bottom 96-well plate and released calcein was quantitated using a fluorescence multiwell plate reader (Cytofluor 2, Perspective, Biosystems, Cambridge Mass.; excitation wavelength 485 nm, emission wavelength 530 nm). Replicate wells were incubated with lysis buffer (50 mM sodium borate, 0.1% Triton X-100, pH 9.0) to determine maximum release or without complement treatment to determine spontaneous release. Percent specific lysis was calculated as [(sample release-spontaneous release)/(maximal release -spontaneous release)]×100%. Percent cytoprotection was calculated as [(percent specific lysis in the present of IL-11/ percent specific lysis in the absence of IL-11)×100. Spontaneous release was generally <25%.

Generation of Allospecific CTLs and CTL Killing Assay:

Alloreactive class I-restricted CD8+ T cells lines were produced as described elsewhere from peripheral blood CD8+ T cells. Biedermann, B. C. and J. S. Pober (1998) [In Process Citation]. J. Immunol. 161:4679–4687. To determine percent lysis, target HUVECs were loaded calcein as described above and incubated overnight. IL-11 in media or media alone were added for an addition of 6 h, after which cells were washed twice with Medium 199, 5% FBS, 5 mM HEPES, 2 mM L-glutamine, 100 u/ml penicillin, 100 μg/ml streptomycin. Effector CTL cells were added in a total volume of 150 μl/well at a predetermined effector/target ratio of 30:1. Replicate wells were incubated with lysis buffer (50 mM sodium borate, 0.1% Triton X-100, pH 9.0) to determine maximum release or without CTL to determine spontaneous release. After 4 h incubation at 37EC, released calcein was measured as described above. Percent cytoprotection was calculated as described above. Spontaneous release was generally <25%.

EXAMPLES

Example 1

Dose and Time Dependent Phosphorylation by IL-11

4 μg of total RNA from cultured HUVECs, CACO-2 or K562 cells was incubated over night with probes for human IL-11Rα chain and GAPDH genes. Samples were digested with RnbaseA/T1 and protected fragments (321 bp for IL-11Rα and 96 bp for GAPDH were resolved on a 6% acylamide/TBE-Urea gel. Lysates from either HUVECs or K562 cells were resolved on SDS-PAGE as described above and immunoblotted with specific antibody to IL-11 receptor α chain. The IL-11 receptor α chain was detected in HUVECs and K562 cells at about MW 83 kD.

Next, HUVECs were either untreated (control), treated with IL-11 (100 ng/ml), or oncostatin M (20 ng/ml) for 2 min and 10 min. Cell lysates were immunoprecipitated with specific antibody to gp130. Immune complexes were resolved on SDS-PAGE and immunoblotted with a phosphotyrosine specific antibody as described above. The results indicate that IL-11 tyrosine phosphorylates gp130 in HUVECs.

To test whether phosphorylation is dose-dependent, HUVECs were untreated (control), treated with increasing concentrations of IL-11 (0.1, 0.3, 1.0, 3.0, 10.0, 30.0, 90.0, 270.0 ng ml) or treated with increasing concentrations of oncostatin M (60, 125, 250, 500, 1000 ng/ml) for 10 min. Lysates were resolved on SDS-PAGE and immunoblotted with specific antibody to either phospho-STAT3 (P-STAT3), STAT3, phospho-STAT1 (P-STAT1), or STAT1. The results indicate that IL-11 exhibits a dose-dependent phosphorylation of STAT3 and STAT1 in HUVECs.

To test whether phosphorylation is time-dependent, HUVECs were either untreated (control), treated with IL-11 (100 ng/ml), or treated with oncostatin M (200 pg/ml) for 2.5 min, 5 min, 10 min 20 min, 40 min and 60 min. Lysates were resolved on SDS-PAGE and immunoblotted with specific antibody to either phospho-STAT3 (P-STAT3) or phospho-STAT1 (P-STAT1). The results indicated that IL-11 phosphorylation is time-dependent.

Next, the ability of IL-11 to phosphorylate p43 and p44 MAP kinases in a dose- and time-dependent manner was tested. HUVECs were cultured in a M199 media containing 1% FCS for 17 h, after which the media was removed and cells were rested for 2 h in the M199 media containing no FCS. In one experiment, HUVECs were either untreated (control) or treated with increasing concentrations of IL-11 (0.3, 1.0, 10.0, 30.0, 90.0, 270.0, 400.0 ng/ml) for 10 min. In another experiment, HUVECs were either untreated (control) or treated with IL-11 (200 ng/ml) for 5 min, 15 min, 30 min and 40 min, or treated with oncostatin M (OnM) (1 ng/ml) for 40 min. Lysates were resolved on SDS-PAGE and immunoblotted with specific antibody to either phospho-p44/p44 antibody (P42/44) or p42/p44 antibody (p42/p44). The results indicate that IL-11 had the ability to phosphorylate p43 and p44 MAP kinases in a dose- and time-dependent manner.

Finally, the ability of IL-11 to induce the degradation of IκBα_or inhibit the effect of TNF on this response was tested. HUVECs were treated with either 10 ng/ml or 100 ng/ml of IL-11 or with 10 U/ml TNF for 5 and 15 min. Other HUVECs were pretreated with media alone (control) or media containing various doses of IL-11 (0.5, 50, 250, 500 or 1000 ng/ml). After 4 h, cells were stimulated without or with TNF (10 U/ml) for 15 min. Lysates were resolved on 10% SDS-PAGE and immunoblotted with specific antibody to IκBα._Cell lysates from HUVECs pretreated with 500 ng/ml and 5000 ng/ml of IL-11 were run on a separate gel. The results indicate that IL-11 neither induces the degradation of IκBα_nor inhibits the effect of TNF on this response.

Example 2

The IL-11 Receptor Alpha Chain is Expressed on B and T Lymphocytes

Murine B Cells and CD4+ and CD8+ T cells were purified from Balb/c spleens using positive selection with MACS (Magnetic Cell Sorting) Microbeads conjugated to anti-mouse B220, CD4 or CD8 antibodies, as per manufacturers protocol (Miltenyi Biotec, Sunnyvale, Calif.). RNA was extracted from purified cell populations as described above using RNA Stat-60 (Tel-test, Inc., Tex.) as per manufacturer's protocol. RNA was DNase treated (RQ1 DNase, Promega, Madison, Wis.) for 30 min at 37° C., then heat inactivated for 5 min at 75° C. RT-PCR was performed (GeneAmp RNA PCR Kit, Perkin Elmer) using 40 ng RNA (10 ng for GAPDH) and oligo pairs specific for murine GAPDH, IL-11 receptor a chain, IL-10 receptor, IL-6 receptor or gp130, and visualized on an ethidium-stained agarose gel. PCR reactions on RNA samples in the absence of reverse transcriptase were negative for each oligo pair, and served as a control for DNA contamination. The IL-11 receptor alpha chain mRNA was detected in highly purified populations of CD4+, CD8+ and B220+ lymphocytes.

Example 3

IL-11 Increases Antigen Specific Cytolytic Activity in Bulk Spleen Cultures

Seven day splenic bulk cultures from cells treated with IL-2, or IL-2 and IL-11, were serially diluted and added to $1 \times 10^4$ $^{51}$Cr-labelled P815.P1HTR cells, which were pulsed for one hour in the presence or absence of NP peptide. The cells were incubated for 4 hours. Supernatants were harvested, and $^{51}$Cr release was determined. Maximum lysis on the target cells was induced with 2% Triton-X 100. % lysis=[(CPM-spontaneous CPM of NP peptide pulsed targets)/(maximum CPM of NP peptide pulsed targets—spontaneous CPM of NP peptide pulsed targets)]×100. % specific lysis=(% lysis on NP peptide pulsed target cells)–(% lysis of control target cells). The example indicates that IL-11 can significantly enhance the % specific lytic activity of NP peptide-specific cytotoxic T cells. At a 50:1 effector to target cell ratio, a 250% enhancement in % specific lysis is observed in cells treated with IL-2 and IL-11 versus cells treated with IL-2 alone.

Example 4

IL-11 Can Substitute for the Requirement of Exogenous IL-2 in the Generation of Antigen Specific Cytolytic Activity in Bulk Spleen Cultures Seven day splenic bulk cultures from cells treated with muIL-2, muIL-6, or rhIL-11 were serially diluted and added to $1 \times 10^4$ $^{51}$Cr-labelled P815.P1HTR cells, which were pulsed for one hour in the presence or absence of NP peptide. The cells were incubated for 4 hours. Supernatants were harvested, and $^{51}$Cr release was determined. % specific lysis was calculated as described above. The example indicates that IL-11 treatment of cells alone in the absence of exogenous IL-2 can significantly enhance the % lytic activity of NP peptide-specific cytotoxic T cells. At a 50:1 effector to target ratio, a 7 fold increase in % specific lysis is observed between cells treated with IL-11 versus cells treated with no exogenously added cytokines.

Example 5

IL-11 Increases the Number of Influenza Specific IFNγ-Producing Cells

Sterile flat bottom 96 well plates (Costar) were coated with an anti-IFNγ antibody (R46A2, 10 Fg/ml, 50 ul/well) at 37° C. for 2 hrs and blocked with PBS+1%BSA+0.05% Tween 20 at 37° C. for 1 hour and washed with PBS. Serial dilutions of splenic cells diluted in RPMI+10% FCS were added to the plates and incubated for 16 hr at 37° C., and then washed 6 times. Biotinylated anti-IFNγ antibody XGM.1 (1.19 Fg/ml) was added to each well and incubated 90 min at room temperature. Following another 4 washes, streptavidin alkaline phosphatase was added and incubated 1 hr at room temperature. After 4 washes, the plates were developed with a solution of 0.6% low melting agarose in 0.1M 2-amino-2-methyl-1 propanol, pH10.5, containing 1 mg/ml BCIP (5-Bromo-4-Chloro-3-Indonyl phosphate). The plates were incubated for 16 hr at room temperature and then the spots were counted. The example indicates that IL-11 enhances the number of influenza-specific IFN-g producing cytotoxic T cells. Cells treated with either IL-2 and either 10 ng/ml or 100 ng/ml of IL-11 had 2–3.5 fold increased number of IFN-g producing cells compared to cells treated with IL-2 alone.

Example 6

IL-11 Increases IFNγ Production from Influenza Specific CTLs

ELISA plates (EIA capture plates, Costar) were coated with an anti-IFNγ antibody (R46A2, 3 Fg/ml, 50 ul/well) at 4° C. for 16 hr and blocked with THSG (Tris high salt gelatin) at 37° C. for 2 hours and washed 4 times. Serial dilutions of IFNγ control supernatants and of unknown samples diluted in PBS+10% FCS were added to the plates and incubated for 2 hr at room temperature, and then washed 4 times. Biotinylated antibody XGM.1 (1.19 Fg/ml) was added to each well and incubated 90 min at room temperature. Following another 4 washes, peroxide-conjugated Avidin (Vector) was added and incubated 1 hr at room temperature. After 4 washes, the plates were developed with ABTS (Kirkegaard and Perry) for 9 min in the dark and stopped with 1% SDS. The absorbance at 405 nm was determined with a Vmax kinetic microplate reader (Molecular Devices). The example indicates that IL-11 can enhance the amount of IFN-g produced from influenza-specific cytotoxic T cells. 2–4 fold elevated levels of IFN-g were detected in the conditioned medium of cells treated with IL-2 and either 10 ng/ml or 100 ng/ml IL-11.

Example 7

Figure 1:
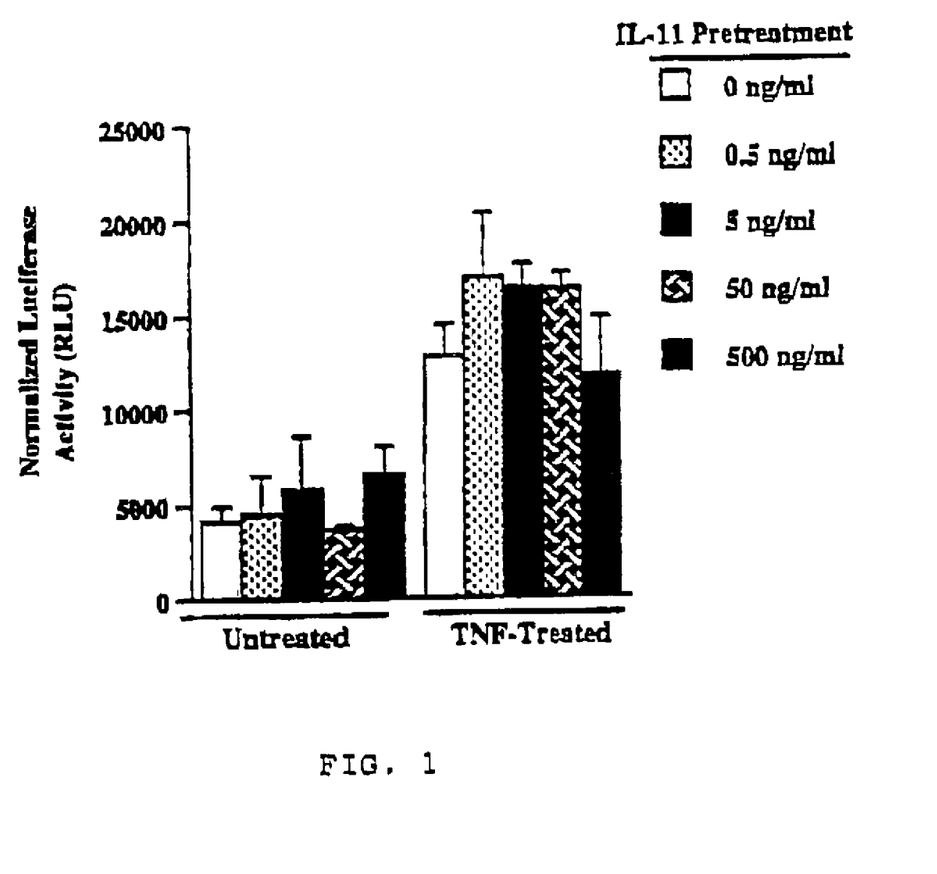
FIG. 1 is a graphic illustration showing the results of the experiment described in Example 7.

IL-11 Does Not Inhibit TNF-Mediated κB-Luciferase Promoter-Reporter Gene Activity HUVECs were transiently cotransfected with κB-luciferase promoter-reporter gene and a β-galactosidase expression construct. Cell were treated with different doses of IL-11 as indicated in FIG. 1. After 4 h, cells were left untreated or treated with 3 U/ml of TNF for 18 h. Luciferase activity was expressed as light units normalized to β-galactosidase activity. Data are presented as the mean +/–s.d. of triplicate in each group from one experiment. Shown in FIG. 1 is one of the three different experiments with similar outcome.

Example 8

IL-11 Treated HUVECs Acquire Resistance Against Complement-Mediated Cytolysis

Figure 2:
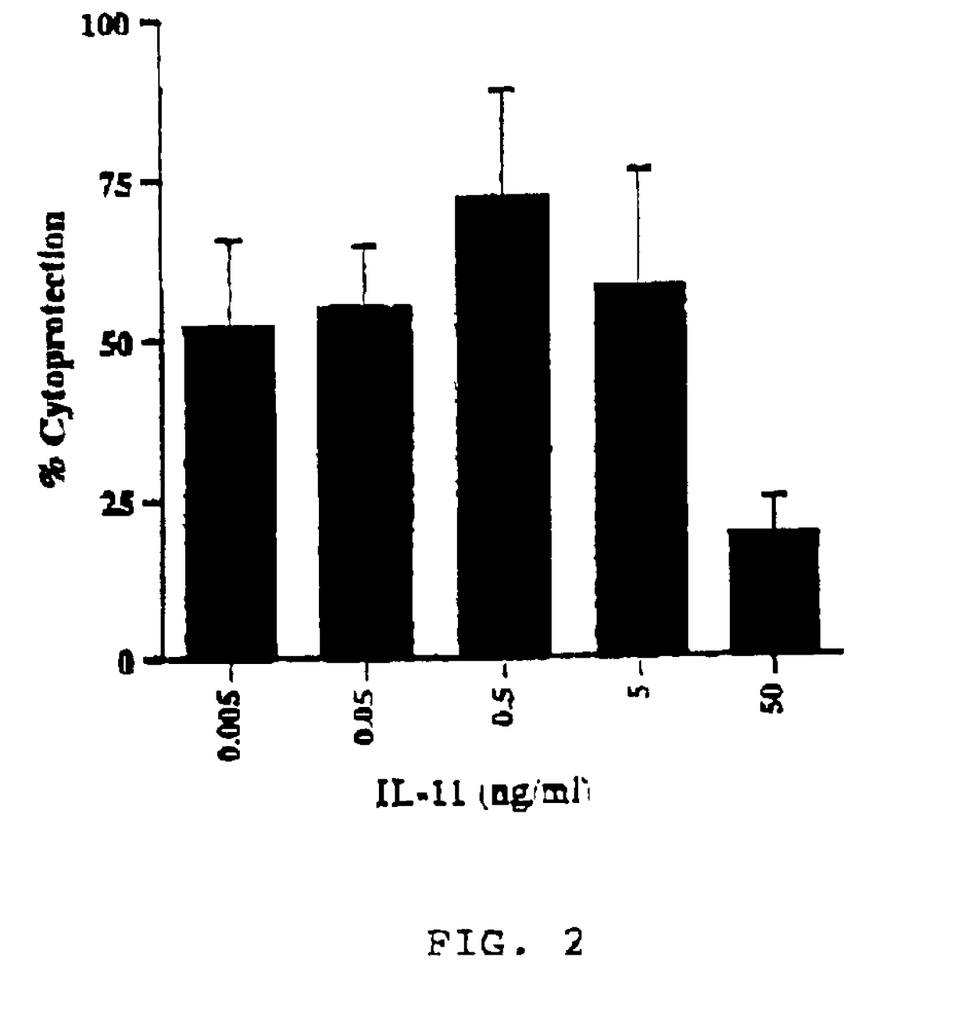
FIG. 2 is a graphic illustration showing the results of the experiment described in Example 8.
Figure 3:
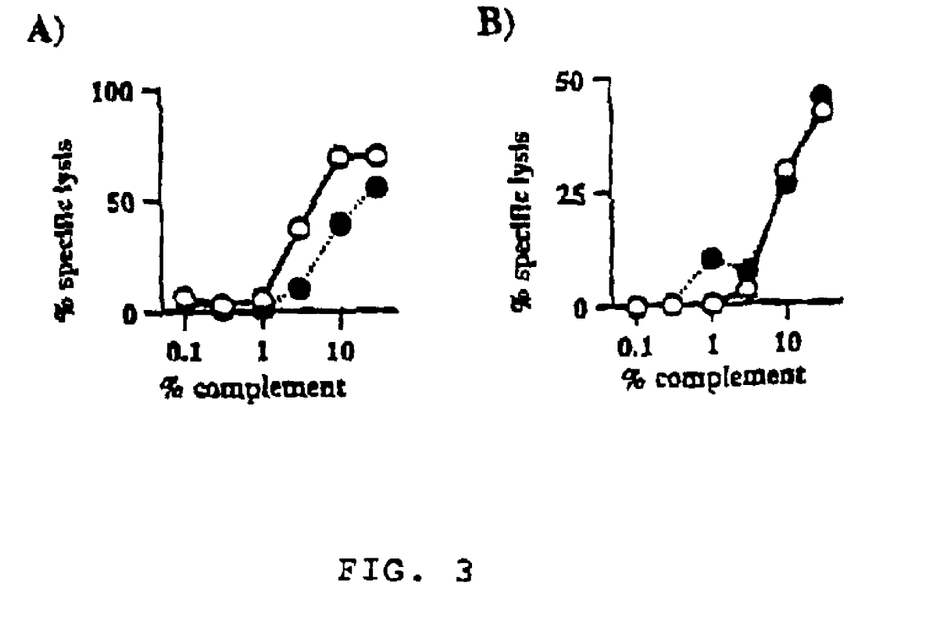
FIG. 3 is a graphic illustration showing the results of the experiment described in Example 9.

Confluent pooled HUVECs were loaded with calcein and treated 6 h with IL-11 at the indicated concentrations. HUVECs were washed and incubated with anti-W6/32 Ab (2.5 µg/ml) followed by addition of baby rabbit complement (25%). After 1 h, supernatant was harvested and released calcein was measured. Percent cytoprotection was calculated as described in Material and Methods. The results are shown in FIG. 2, as the mean +/−s.d. of three different experiments.

Example 9

Cytoprotection of HUVECs by Pretreatment with IL-11 is Protein Synthesis Dependent HUVECs were loaded with calcein, chased and pretreated for 6 hours without (open circles) or with 0.5 ng/ml IL-11 (closed circles) in the presence (panel B) or absence (panel A) of cycloheximide. Cells were washed and incubated with W6/32 (2.5 µg/ml) for 30 min before complement was added at the indicated concentrations. After 1 h, supernatant was harvested and calcein release measured. Percent specific lysis was calculated (see Material and Methods). Maximal and spontaneous release was significantly different for cycloheximide treated cells and controls. These values were therefore determined for the 2 groups separately, and sample release was normalized to these values. Shown is one of the three different experiments with similar outcome.

Example 10

Effect of IL-11 Treatment on E-Selectin and ICAM-1 Expression

HUVECs were treated with either TNF or IL-11 in the amounts indicated in Table 1. Surface levels of E-selectin and ICAM-1 were quantified by indirect immunofluorescence using H4/18 and E16 antibody, respectively. The results are shown in Table 1. The numbers are expressed as corrected mean fluorescence intensity (cMFI) calculated by subtracting the mean fluorescence value for isotype match control antibody (k16/16) from the mean fluorsescence value for either H4/18 or E16 antibody. Results from 2 independent experiments are shown. Il-11 had very little effect on E-selectin or ICAM-1 expression.

|  | EXPERIMENT 1 | | EXPERIMENT 2 | |
| --- | --- | --- | --- | --- |
| TREATMENT | E-selectin (cMFI) | ICAM-1 (cMFI) | E-selectin (cMFI) | ICAM-1 (cMFI) |
| None | 4.8 | 9.3 | 12 | 18.8 |
| TNF (1 U/ml) | 186.2 | 81 | 309.97 | 154 |
| IL-11 (100 ng/ml) | 9.0 | 10.4 | 11.5 | 23.3 |
| IL-11 (1000 ng/ml) | 11.7 | 11 | 12.8 | 15.2 |

Example 11

Effect of IL-11 Treatment on CTL-Mediated Cytolysis

Allospecific CTL clones were generated as described (see Material and Methods). Confluent target HUVECs were treated overnight with IL-11 at the concentrations indicated in Table 2. Calcein-release based CTL assays were run (see Material and Methods) and the results are shown in Table 2. Results from 3 independent experiments are shown.

TABLE 2

| | Percent Cytoprotection | | | |
| --- | --- | --- | --- | --- |
| IL-11 (ng/ml) | 0.5 | 5 | 50 | 500 |
| Experiment 1 | 64 | n.d. | 22 | n.d. |
| Experiment 2 | n.d. | 75 | 58 | 17 |
| Experiment 3 | 60 | 50 | 40 | n.d. |

Example 12

Effect of IL-11 on Class I MHC Expression

After overnight treatment with 50 ng/ml IL-11 or 100 ng/ml IFNγ or a combination of 50 mg/ml IL-11 and 100 ng/ml IFNγ, HUVECs were trypsinized and stained for class I MHC. The results are shown in Table 3. Results from 2 separate experiments are shown. IL-11 does not affect class I MHC expression on HUVECs.

TABLE 3

| | Class I-MHC Expression (cMFI) | |
| --- | --- | --- |
| TREATMENT | Experiment 1 | Experiment 2 |
| none | 93 | 90 |
| IL-11 | 92 | 93 |
| IFNγ | 130 | 126 |
| IL-11 + IFNγ | 127 | 130 |

While the present invention has been described in terms of specific methods and compositions, it is understood that variations and modifications will occur to those skilled in the art upon consideration of the present invention. Numerous modifications and variations in the invention as described in the above illustrative examples are expected to occur to those skilled in the art and, consequently, only such limitations as appear in the appended claims should be placed thereon. Accordingly, it is intended in the appended claims to cover all such equivalent variations which come within the scope of the invention as claimed.

REFERENCE

1. Weich, N. S., A. Wang, M. Fitzgerald, T. Y. Neben, D. Donaldson, J. Giannotti, J. Yetz-Aldape, R. M. Leven, and K. J. Turner. 1997. Recombinant human interleukin-11 directly promotes megakaryocytopoiesis in vitro. Blood. 90:3893–3902.
2. Orazi, A., R. J. Cooper, J. Tong, M. S. Gordon, L. Battiato, G. W. Sledge, Jr., J. A. Kaye, M. Kahsai, and R. Hoffman. 1996. Effects of recombinant human interleukin-11 (Neumega rhIL-11 growth factor) on megakaryocytopoiesis in human bone marrow. Exp. Hematol. 24:1289–1297.
3. de Haan, G., B. Dontje, C. Engel, M. Loeffler, and W. Nijhof. 1995. In vivo effects of interleukin-11 and stem cell factor in combination with erythropoietin in the regulation of erythropoiesis. Br. J. Haematol. 90:783–790.
4. Kaye, J. A. 1996. Clinical development of recombinant human interleukin-11 to treat chemotherapy-induced thrombocytopenia. Curr. Opin. Hematol. 3:209–215.
5. Du, X., Q. Liu, Z. Yang, A. Orazi, F. J. Rescorla, J. L. Grosfeld, and D. A. Williams. 1997. Protective effects of interleukin-11 in a murine model of ischemic bowel necrosis. Am. J. Physiol. 272:G545-G552.
6. Orazi, A., X. Du, Z. Yang, M. Kashai, and D. A. Williams. 1996. Interleukin-11 prevents apoptosis and accelerates recovery of small intestinal mucosa in mice treated with combined chemotherapy and radiation. Lab. Invest. 75:33–42.

7. Keith, J. C., Jr., L. Albert, S. T. Sonis, C. J. Pfeiffer, and R. G. Schaub. 1994. IL-11, a pleiotropic cytokine: exciting new effects of IL-11 on gastrointestinal mucosal biology. Stem. Cells. (Dayt). 12 Suppl 1:79–89.
8. Qiu, B. S., C. J. Pfeiffer, and J. C. Keith, Jr. 1996. Protection by recombinant human interleukin-11 against experimental TNB-induced colitis in rats. Dig. Dis. Sci. 41:1625–1630.
9. Hill, G. R., K. R. Cooke, T. Teshima, J. M. Crawford, J. C. Keith, Jr., Y. S. Brinson, D. Bungard, and J. L. Ferrara. 1998. Interleukin-11 promotes T cell polarization and prevents acute graft-versus-host disease after allogeneic bone marrow transplantation. J. Clin. Invest 102:115–123.
10. Redlich, C. A., X. Gao, S. Rockwell, M. Kelley, and J. A. Elias. 1996. IL-11 enhances survival and decreases TNF production after radiation-induced thoracic injury. J. Immunol. 157:1705–1710.
11. Waxman, A. B., O. Einarsson, T. Seres, R. G. Knickelbein, J. B. Warshaw, R. Johnston, R. J. Homer, and J. A. Elias. 1998. Targeted lung expression of interleukin-11 enhances murine tolerance of 100% oxygen and diminishes hyperoxia-induced DNA fragmentation. J. Clin. Invest. 101:1970–1982.
12. Leng, S. X. and J. A. Elias. 1997. Interleukin-11 inhibits macrophage interleukin-12 production. J. Immunol. 159:2161–2168.
13. Trepicchio, W. L., L. Wang, M. Bozza, and A. J. Dorner. 1997. IL-11 regulates macrophage effector function through the inhibition of nuclear factor-kappaB. J. Immunol. 159:5661–5670.
14. Trepicchio, W. L., M. Bozza, G. Pedneault, and A. J. Dorner. 1996. Recombinant human IL-11 attenuates the inflammatory response through down-regulation of proinflammatory cytokine release and nitric oxide production. J. Immunol. 157:3627–3634.
15. Taga, T. and T. Kishimoto. 1997. Gp130 and the interleukin-6 family of cytokines. Annu. Rev. Immunol. 15:797–819.
16. Zhang, X. G., J. J. Gu, Z. Y. Lu, K. Yasukawa, G. D. Yancopoulos, K. Turner, M. Shoyab, T. Taga, T. Kishimoto, R. Bataille, and et al. 1994. Ciliary neurotropic factor, interleukin 11, leukemia inhibitory factor, and oncostatin M are growth factors for human myeloma cell lines using the interleukin 6 signal transducer gp130. J. Exp. Med. 179:1337–1342.
17. Yang, Y. C. and T. Yin. 1995. Interleukin (IL)-11—mediated signal transduction. Ann. N. Y. Acad. Sci. 762:31–40.
18. Nandurkar, H. H., D. J. Hilton, P. Nathan, T. Willson, N. Nicola, and C. G. Begley. 1996. The human IL-11 receptor requires gp130 for signalling: demonstration by molecular cloning of the receptor. Oncogene. 12:585–593.
19. Miyatake, T., K. Sato, K. Takigami, N. Koyamada, W. W. Hancock, H. Bazin, D. Latinne, F. H. Bach, and M. P. Soares. 1998. Complement-fixing elicited antibodies are a major component in the pathogenesis of xenograft rejection. J. Immunol. 160:4114–4123.
20. Yin, T., K. Yasukawa, T. Taga, T. Kishimoto, and Y. C. Yang. 1994. Identification of a 130-kilodalton tyrosine-phosphorylated protein induced by interleukin-11 as JAK2 tyrosine kinase, which associates with gp130 signal transducer. Exp. Hematol. 22:467–472.
21. Wang, X. Y., D. K. Fuhrer, M. S. Marshall, and Y. C. Yang. 1995. Interleukin-11 induces complex formation of Grb2, Fyn, and JAK2 in 3T3L1 cells. J. Biol. Chem. 270:27999–28002.
22. Lutticken, C., U. M. Wegenka, J. Yuan, J. Buschmann, C. Schindler, A. Ziemiecki, A. G. Harpur, A. F. Wilks, K. Yasukawa, T. Taga, and et al. 1994. Association of transcription factor APRF and protein kinase Jak1 with the interleukin-6 signal transducer gp130. Science 263:89–92.
23. Hemmann, U., C. Gerhartz, B. Heesel, J. Sasse, G. Kurapkat, J. Grotzinger, A. Wollmer, Z. Zhong, J. E. Darnell, Jr., L. Graeve, P. C. Heinrich, and F. Horn. 1996. Differential activation of acute phase response factor/Stat3 and Stat1 via the cytoplasmic domain of the interleukin 6 signal transducer gp130. II. Src homology SH2 domains define the specificity of stat factor activation. J. Biol. Chem. 271:12999–13007.
24. Zhong, Z., Z. Wen, and J. E. Darnell, Jr. 1994. Stat3: a STAT family member activated by tyrosine phosphorylation in response to epidermal growth factor and interleukin-6. Science 264:95–98.
25. Ihle, J. N. 1996. STATs: signal transducers and activators of transcription. Cell 84:331–334.
26. Akira, S. 1997. IL-6-regulated transcription factors. Int. J. Biochem. Cell Biol. 29:1401–1418.
27. Zhang, X., J. Blenis, H. C. Li, C. Schindler, and S. Chen-Kiang. 1995. Requirement of serine phosphorylation for formation of STAT-promoter complexes. Science 267:1990–1994.
28. Boulton, T. G., Z. Zhong, Z. Wen, J. E. Darnell, Jr., N. Stahl, and G. D. Yancopoulos. 1995. STAT3 activation by cytokines utilizing gp130 and related transducers involves a secondary modification requiring an H7-sensitive kinase. Proc. Natl. Acad. Sci. U. S. A. 92:6915–6919.
29. Adunyah, S. E., G. C. Spencer, R. S. Cooper, J. A. Rivero, and K. Ceesay. 1995. Interleukin-11 induces tyrosine phosphorylation, and c-jun and c-fos mRNA expression in human K562 and U937 cells. Ann. N. Y. Acad. Sci. 766:296–299.
30. Yin, T. and Y. C. Yang. 1994. Mitogen-activated protein kinases and ribosomal S6 protein kinases are involved in signaling pathways shared by interleukin-11, interleukin-6, leukemia inhibitory factor, and oncostatin M in mouse 3T3-L1 cells. J. Biol. Chem. 269:3731–3738.
31. Gimbrone, M. A., Jr. 1976. Culture of vascular endothelium. Prog. Hemost. Thromb. 3:1–28.
32. Thornton, S. C., S. N. Mueller, and E. M. Levine. 1983. Human endothelial cells: use of heparin in cloning and long-term serial cultivation. Science 222:623–625.
33. Karmann, K., W. Min, W. C. Fanslow, and J. S. Pober. 1996. Activation and homologous desensitization of human endothelial cells by CD40 ligand, tumor necrosis factor, and interleukin 1. J. Exp. Med. 184:173–182.
34. Min, W., S. Ghosh, and P. Lengyel. 1996. The interferon-inducible p202 protein as a modulator of transcription: inhibition of NF-kappa B, c-Fos, and c-Jun activities. Mol. Cell Biol. 16:359–368.
35. Biedermann, B. C. and J. S. Pober. 1998. Human endothelial cells induce and regulate cytolytic T cell differentiation. J. Immunol. 161:4679–4687.
36. Sierra-Honigmann, M. R., A. K. Nath, C. Murakami, G. Garcia-Cardena, A. Papapetropoulos, W. C. Sessa, L. A. Madge, J. S. Schechner, M. B. Schwabb, P. J. Polverini, and J. R. Flores-Riveros. 1998. Biological action of leptin as an angiogenic factor. Science 281:1683–1686.
37. Faris, M., B. Ensoli, N. Kokot and A. E. Nel. 1998. Inflammatory cytokines induce the expression of basic fibroblast growth factor (bFGF) isoforms required for the growth of Kaposi's sarcoma and endothelial cells through the activation of AP-1 response elements in the bFGF promoter. AIDS 12:19–27.

38. Brown, T. J., J. M. Rowe, J. W. Liu, and M. Shoyab. 1991. Regulation of IL-6 expression by oncostatin M. J. Immunol. 147:2175–2180.
39. Modur, V., M. J. Feldhaus, A. S. Weyrich, D. L. Jicha, S. M. Prescott, G. A. Zimmerman, and T. M. McIntyre. 1997. Oncostatin M is a proinflammatory mediator. In vivo effects correlate with endothelial cell expression of inflammatory cytokines and adhesion molecules. J. Clin. Invest. 100:158–168.
40. Yao, L., J. Pan, H. Setiadi, K. D. Patel, and R. P. McEver. 1996. Interleukin 4 or oncostatin M induces a prolonged increase in P-selectin mRNA and protein in human endothelial cells. J. Exp. Med. 184:81–92.
41. Cherel, M., M. Sorel, B. Lebeau, S. Dubois, J. F. Moreau, R. Bataille, S. Minvielle, and Y. Jacques. 1995. Molecular cloning of two isoforms of a receptor for the human hematopoietic cytokine interleukin-11. Blood. 86:2534–2540.
42. Lebeau, B., F. A. Montero Julian, J. Wijdenes, G. Muller-Newen, H. Dahmen, M. Cherel, P. C. Heinrich, H. Brailly, M. M. Hallet, A. Godard, S. Minvielle, and Y. Jacques. 1997. Reconstitution of two isoforms of the human interleukin-11 receptor and comparison of their functional properties. FEBS Lett. 407:141–147.
43. Frasca, D., C. Pioli, F. Guidi, S. Pucci, M. Arbitrio, G. Leter, and G. Doria. 1996. IL-11 synergizes with IL-3 in promoting the recovery of the immune system after irradiation [see comments]. Int. Immunol. 8:1651–1657.
44. Schieven, G. L., J. C. Kallestad, T. J. Brown, J. A. Ledbetter, and P. S. Linsley. 1992. Oncostatin M induces tyrosine phosphorylation in endothelial cells and activation of p62yes tyrosine kinase. J. Immunol. 149:1676–1682.
45. Ghosh, S., M. J. May, and E. B. Kopp. 1998. NF-kappa B and Rel proteins: evolutionarily conserved mediators of immune responses. Annu. Rev. Immunol. 16:225–260.
46. Wang, C. Y., M. W. Mayo, R. G. Korneluk, D. V. Goeddel, and A. S. Baldwin, Jr. 1998. NF-kappaB antiapoptosis: induction of TRAF1 and TRAF2 and c-IAP1 and c-IAP2 to suppress caspase-8 activation. Science 281:1680–1683.
47. Van Antwerp, D. J., S. J. Martin, I. M. Verma, and D. R. Green. 1998. Inhibition of TNF-induced apoptosis by NF-kappa B. Trends. Cell Biol. 8:107–111.
48. Collins, T., M. A. Read, A. S. Neish, M. Z. Whitley, D. Thanos, and T. Maniatis. 1995. Transcriptional regulation of endothelial cell adhesion molecules: NF-kappa B and cytokine-inducible enhancers. FASEB. J. 9:899–909.
49. Johnson, D. R., I. Douglas, A. Jahnke, S. Ghosh, and J. S. Pober. 1996. A sustained reduction in IkappaB-beta may contribute to persistent NF-kappaB activation in human endothelial cells. J. Biol. Chem. 271:16317–16322.
50. Pober, J. S. and R. S. Cotran. 1990. The role of endothelial cells in inflammation. Transplantation. 50:537–544.
51. Renne, C., K. J. Kallen, J. Mullberg, T. Jostock, J. Grotzinger, and S. Rose-John. 1998. A new type of cytokine receptor antagonist directly targeting gp130. J. Biol. Chem. 273:27213–27219.
52. Auguste, P., C. Guillet, M. Fourcin, C. Olivier, J. Veziers, A. Pouplard-Barthelaix, and H. Gascan. 1997. Signaling of type II oncostatin M receptor. J. Biol. Chem. 272:15760–15764.
53. Romano, M., M. Sironi, C. Toniatti, N. Polentarutti, P. Fruscella, P. Ghezzi, R. Faggioni, W. Luini, V. van Hinsbergh, S. Sozzani, F. Bussolino, V. Poli, G. Ciliberto, and A. Mantovani. 1997. Role of IL-6 and its soluble receptor in induction of chemokines and leukocyte recruitment. Immunity. 6:315–325.
54. Shresta, S., C. T. Pham, D. A. Thomas, T. A. Graubert, and T. J. Ley. 1998. How do cytotoxic lymphocytes kill their targets? Curr. Opin. Immunol. 10:581–587.
55. Richardson, B. C., N. D. Lalwani, K. J. Johnson, and R. M. Marks. 1994. Fas ligation triggers apoptosis in macrophages but not endothelial cells. Eur. J. Immunol. 24:2640–2645.
56. Shinkai, Y., K. Takio, and K. Okumura. 1988. Homology of perforin to the ninth component of complement (C9). Nature 334:525–527.
57. Krahenbuhl, O. and J. Tschopp. 1990. Involvement of granule proteins in T-cell-mediated cytolysis. Nat. Immun. Cell Growth. Regul. 9:274–282.

What is claimed:

1. A method of reducing complement-mediated cytotoxicity in a mammal which comprises identifying a mammal at risk of developing complement-mediated cytotoxicity; and administering to said mammal, prior to tissue transplantation, a therapeutically effective amount of interleukin-11, wherein said amount of IL-11 reduces complement-mediated cytotoxicity in said mammal.

2. The method of claim 1, wherein the therapeutically effective amount of interleukin-11 comprises 1 to 100 tag/kg body weight.

3. The method of claim 1 wherein said mammal is a human.

4. A method of ameliorating complement-mediated cytotoxicity in a mammal which comprises identifying a mammal at risk of developing complement-mediated cytotoxicity; and administering, at the time of tissue transplantation, a therapeutically effective amount of interleukin-11, wherein said amount of IL-11 ameliorates complement-mediated cytotoxicity in said mammal.

5. The method of claim 4, wherein the therapeutically effective amount of interleukin-11 comprises 1 to 100 $\mu$g/kg body weight.

6. The method of claim 4, wherein the interleukin-11 is administered daily until improvement of the complement-mediated cytotoxicity disorder is observed.

7. The method of claim 4, wherein the interleukin-11 is administered daily until remission of the complement-mediated disorder is observed.

8. The method of claim 4, wherein said mammal is a human.

9. The method of claim 3, wherein the interleukin-11 is administered for three days beginning on the day of the tissue transplant.

10. The method of claim 9, wherein the therapeutically effective amount of interleukin-11 comprises 1 to 100 $\mu$g/kg body weight.

11. A method of treating complement-mediated cytotoxicity associated with organ or tissue transplantation in a mammal which comprises administering to said mammal a therapeutically effective amount of interleukin-11, wherein said amount of IL-11 reduces complement-mediated cytotoxicity in said mammal.

12. The method of claim 11, wherein the therapeutically effective amount of interleukin-11 comprises 1 to 100 $\mu$g/kg body weight.

* * * * *

UNITED STATES PATENT AND TRADEMARK OFFICE
CERTIFICATE OF CORRECTION

PATENT NO. : 6,953,777 B2
DATED : October 11, 2005
INVENTOR(S) : James Keith, Joseph M. Carroll and Jordan S. Pober It is certified that error appears in the above-identified patent and that said Letters Patent is hereby corrected as shown below:

Column 22,
Line 28, "tag/kg" should read -- $\mu$g/kg --.

Signed and Sealed this

Seventh Day of March, 2006

JON W. DUDAS
*Director of the United States Patent and Trademark Office*